United States Patent [19]
Birmingham et al.

[11] Patent Number: 6,062,392
[45] Date of Patent: May 16, 2000

[54] MICROMACHINED VIRTUAL IMPACTOR

[75] Inventors: Joseph G. Birmingham; Patrick T. Call, both of Richland; Vanessa M. Kenning; Alireza Shekarriz, both of Kennewick; Charles J. Call, Pasco, all of Wash.

[73] Assignee: MesoSystems Technology, Inc., Richland, Wash.

[21] Appl. No.: 09/191,980

[22] Filed: Nov. 13, 1998

[51] Int. Cl.⁷ .............................. B07B 7/04; B01D 45/08; B01D 53/00
[52] U.S. Cl. .......................... 209/143; 209/134; 209/139; 55/462; 95/32
[58] Field of Search .................................... 209/143, 134, 209/135, 142, 146, 147; 95/32, 33; 55/462

[56] References Cited

U.S. PATENT DOCUMENTS

| | | |
|---|---|---|
| 877,460 | 1/1908 | Brunner et al. . |
| 902,958 | 11/1908 | Galusha . |
| 906,038 | 12/1908 | Terry . |
| 1,603,878 | 10/1926 | Smith . |
| 1,807,378 | 5/1931 | Budil . |
| 1,825,274 | 9/1931 | Leach . |
| 2,939,545 | 6/1960 | Silverman . |
| 3,693,457 | 9/1972 | Pilat . |
| 3,754,868 | 8/1973 | Witz et al. . |
| 3,901,798 | 8/1975 | Peterson . |

(List continued on next page.)

FOREIGN PATENT DOCUMENTS

| | | |
|---|---|---|
| 0 543 108 A1 | 5/1993 | European Pat. Off. . |
| 626 191 | 8/1927 | France . |
| 13 10 931 U | 9/1934 | Germany . |
| 2 260 729 | 5/1974 | Germany . |
| WO 98/58725 | 12/1998 | WIPO .......................................... 45/8 |

OTHER PUBLICATIONS de la Mora, J.F., "Aerodynamic Focusing of Particles and Heavy Molecules, First Annual Report," NTIS, Feb. 16, 1988, 16 pages.

de la Mora, J.F., "Aerodynamic Focusing of Particles and Heavy Molecules. Final Report," NTIS, Jan. 8, 1990, 12 pages.

de la Mora, J.F., "Drastic Improvement of the Resolution of Aerosol Size Spectrometers via Aerodynamic Focusing: The Case of Variable–Pressure Impactors," *Chemical Engineering Communications*, vol. 151, 1996, pp. 101–124.

de la Mora, J.F., et al., "Aerodynamic Focusing of Particles in a Carrier Gas," *Journal of Fluid Mechanics*, vol. 195, Oct. 1988, pp. 1–21.

(List continued on next page.)

*Primary Examiner*—Donald P. Walsh
*Assistant Examiner*—Brett C. Martin
*Attorney, Agent, or Firm*—Ronald M. Anderson

[57] ABSTRACT

A separation plate (10) includes a first surface and an opposing second surface. Plural pairs of a nozzle (14) and a virtual impactor (16) are provided on the first surface. Each nozzle tapers from an inlet end (14a) to an outlet end (14b). Each virtual impactor comprises a pair of generally fin-shaped projections (24). Each fin-shaped projection includes an inner wall (26) and a convex outer wall (28). The inner walls of the fin-shaped projections of a virtual impactor face each other to define a minor flow passage (30) therebetween. The convex outer walls of the fin-shaped projections of a virtual impactor cooperatively present a convex surface including a virtual impact void therethrough. The virtual impact void defines an inlet end of the minor flow passage. A virtual impactor body (33) is provided between adjacent virtual impactors (16). When a particle-laden fluid stream (23) is caused to flow through the nozzles and advance to the virtual impactors, a major portion of the fluid containing a minor portion of particles flows around the virtual impactors, is blocked by the virtual impactor bodies, and redirected from the first surface through a suitable major flow outlet. A minor portion of the fluid containing a major portion of particles enters the virtual impact voids, advances through the minor flow passages, and exits therefrom, where it can be collected, analyzed, or processed further in any other manner.

26 Claims, 5 Drawing Sheets

U.S. PATENT DOCUMENTS

| | | |
|---|---|---|
| 3,932,151 | 1/1976 | Lau . |
| 3,983,743 | 10/1976 | Olin et al. . |
| 4,133,202 | 1/1979 | Marple . |
| 4,301,002 | 11/1981 | Loo ......................................... 209/143 |
| 4,321,822 | 3/1982 | Marple et al. . |
| 4,387,603 | 6/1983 | Nelson . |
| 4,452,068 | 6/1984 | Loo . |
| 4,640,140 | 2/1987 | Burghoffer et al. . |
| 4,670,135 | 6/1987 | Marple et al. . |
| 4,689,052 | 8/1987 | Ogren et al. . |
| 4,697,462 | 10/1987 | Daube, Jr. et al. . |
| 4,764,186 | 8/1988 | Langer . |
| 4,767,524 | 8/1988 | Yeh et al. . |
| 4,877,430 | 10/1989 | Gutermuth . |
| 4,941,899 | 7/1990 | Liu . |
| 4,942,297 | 7/1990 | Johnson et al. . |
| 4,972,957 | 11/1990 | Liu et al. ............................... 209/143 |
| 4,990,740 | 2/1991 | Meyer . |
| 5,040,424 | 8/1991 | Marple et al. . |
| 5,128,539 | 7/1992 | Rodgers et al. . |
| 5,254,861 | 10/1993 | Carpenter et al. . |
| 5,318,609 | 6/1994 | Kittler . |
| 5,332,550 | 7/1994 | Booker . |
| 5,412,975 | 5/1995 | Raabe et al. . |
| 5,425,802 | 6/1995 | Burton et al. . |
| 5,472,645 | 12/1995 | Rock et al. . |
| 5,498,271 | 3/1996 | Marple et al. . |
| 5,512,216 | 4/1996 | Rock et al. . |
| 5,533,406 | 7/1996 | Geise . |
| 5,788,741 | 8/1998 | Burton et al. ............................. 95/32 |
| 5,858,043 | 1/1999 | Geise .................................. 209/143 X |
| 5,967,332 | 10/1999 | Willeke ............................. 209/134 X |

OTHER PUBLICATIONS

Fernandez–Feria, R., et al., "Brownian–Motion Limited Aerodynamic Focusing of Heavy Molecules," Rarefied Gas Dynamics, Beylich, A.E., Ed., Proceedings of the 17th International Symposium on Rarefied Gas Dynamics, Jul. 8–14, 1990, pp. 214–221.

Fuerstenau, S., et al., "Visualization of Aerodynamically Focused Subsonic Aerosol Jets," *Journal of Aerosol Science*, vol. 25, No. 1, Jan. 1994, pp. 165–173.

Hochrainer, D., Institut für Aerobiologie, "Measurement of Aerosol Particle Size Distribution with an Improved Spectral Impactor," NTIS No. N7323533, 1973, 26 pages.

Jurcik, B., et al., "On the Shape of Impactor Efficiency Curves," *Journal of Aerosol Science*, vol. 26, No. 7, 1995, pp. 1139–1147.

Liu, P., et al., "Optimizing the Detection Efficiency of a Low Pressure, In–Situ Particle Monitor Using Aerodynamic Focusing Lenses," *Proceedings—Institute of Environmental Sciences*, 1996, pp. 217–224.

Patent Cooperation Treaty Search Report PCT–US98–12471, Corona Catalysis Corporation et al., Oct. 14, 1998.

Vance, Richard F., "Slanted Baffle Mist Eliminator", *U.S. Statutory Invention*, Registration No. H1499, Nov. 7, 1995.

MICROMACHINED VIRTUAL IMPACTOR

This invention was made with government support under Contract DAAM01-97-M-0006 awarded by the U.S. Department of Defense. The government has certain rights in this invention.

FIELD OF THE INVENTION

This invention pertains to the field of separating particles from a fluid stream, and more particularly to a combination of nozzles and virtual impactor projections that is used to separate a particle-laden fluid stream into a major portion containing a minor portion of particles and a minor portion containing a major portion of particles.

BACKGROUND OF THE INVENTION

The separation and collection of particles/aerosols from an airstream or other fluid streams are of concern in two contexts: first, in analyzing the type and concentration of such particles/aerosols and, second, in cleaning the fluid stream for subsequent use. Additionally, there are occasions in both cases where classification of particles by size is desired. For example, the detection of airborne biological or chemical warfare agents, the detection of biological contamination in confined spaces, such as aircraft or hospitals, or the detection of industrial pollutants (either in ambient fluid or in smokestacks) may be required in various scenarios.

Much effort has been expended in the past in the detection and classification of particles or aerosols in fluid streams. Impactors have been used for collecting aerosol particles for many decades. In the earliest embodiments, a stream of fluid containing the particles was accelerated toward an impactor plate. Due to their inertia, the particles hit the impactor plate and were collected there while the fluid was deflected to the side. With these types of impactors, only heavy particles were collected while particles below a certain "cut size" were carried away by the fluid stream.

However, a significant cause of inaccuracy in such impactors results from the deposition of particles on surfaces of the impactor other than the intended collection surfaces. This phenomenon reduces the accuracy of measurement of total particle mass concentration and of the size-fractionation of particles, since such losses cannot be accurately estimated for aerosols having varying size, shape, or chemistry. Additionally, particles may either reentrain in the fluid stream or bounce from the impactor's collection surface upon impact.

To remedy this problem "virtual" impactors have been developed that separate particles from a fluid stream by forces other than impaction. Virtual impactors may operate on a number of different principles, but all avoid actual "impact" and rely on differences in particle mass to induce inertial separation. Specifically, a particle-laden fluid stream is directed toward a surface presenting an obstruction to the forward movement of the fluid stream. The surface includes a void at the point where the particles would normally impact the surface. When a major portion of the fluid stream changes direction to avoid the obstruction presented by the surface, fine particles remain entrained in the deflected major portion of the fluid stream. Heavier or more dense particles, on the other hand, fail to change direction and are collected in a region of relatively stagnant fluid (a "dead air zone") that is created near the surface. The heavier particles entrained in a minor portion of the fluid stream enter the void defined through the surface, where they can be captured or analyzed.

Some examples of virtual impactors can be found in U.S. Pat. Nos. 3,901,798; 4,670,135; 4,767,524; 5,425,802; and 5,533,406. Because typical virtual impactors do not actually collect particles themselves, but merely redirect them into two different fluid streams according to their mass, they are essentially free of the problems of particle bounce and reentrainment associated with actual impactor devices. Still, particle "wall loss", i.e., unintended deposition of particles on various surfaces of virtual impactor structures, especially at curved or bent portions, remains a challenge with many virtual impactors because typically many stages or layers of virtual impactors are required to complete particle separation.

A need exists for a virtual impactor that separates particles from a fluid stream more efficiently and specifically without substantial particle wall loss.

SUMMARY OF THE INVENTION

The present invention provides a separation plate for efficiently separating particles from a fluid stream. The separation plate includes a first surface and an opposing second surface. The first surface is provided with plural pairs of a nozzle and a virtual impactor. Each nozzle includes an inlet end and an outlet end, and generally tapers from the inlet end to the outlet end. Each virtual impactor comprises a pair of generally fin-shaped projections. Each fin-shaped projection includes an inner wall and a convex outer wall. Two inner walls of the fin-shaped projections in a pair are spaced apart and face each other to define an upstream minor flow passage therebetween. Two convex outer walls of the fin-shaped projections in a pair cooperatively present a generally convex leading surface. The convex surface includes a virtual impact void that defines an inlet end of the upstream minor flow passage. The convex surface faces the outlet end of each nozzle such that the nozzle and the upstream minor flow passage are aligned. The first surface may also include a plurality of virtual impactor bodies extending downstream from the downstream ends of adjacent fin-shaped projections of adjacent pairs of virtual impactors. Each virtual impactor body includes opposing external walls. External walls of adjacent virtual impactor bodies are spaced apart to define a downstream minor flow passage therebetween. The upstream and downstream minor flow passages are aligned and communicate with each other to together define a minor flow passage. A suitable major flow outlet is provided adjacent the virtual impactor body. For example, the virtual impactor body may include an orifice therethrough or adjacent thereto. The orifice defines a terminal end of a passageway that extends through the separation plate to communicate with the second surface.

In operation, particle-laden fluid streams are caused to flow along the first surface of the separation plate, and enter the inlet ends of the nozzles. The fluid streams exit the nozzles from the outlet ends, and advance toward the convex surfaces of the virtual impactors. The nozzles serve to lessen the fluid turbulence and preferably laminarize the fluid flow. A major portion of the fluid streams containing a minor portion of the particles (hereinafter "major flow) changes direction to avoid the obstructions presented by the convex surfaces, and flows toward the virtual impactor bodies. The major flow enters the orifices and flows through the passageways to the second surface of the separation plate, where it can be exhausted or processed further. A minor portion of the fluid streams containing a major portion of the particles (hereinafter "minor flow") fails to negotiate turns around the convex surfaces, enters the virtual impact voids defined through the convex surfaces, advances through the minor flow passages along the first surface and exits therefrom, where it can be collected or processed further. Accordingly, the separation plate separates a particle-laden fluid stream into a minor flow on the first surface and a major flow on the second surface. Since a minor flow does not experience any deflection, the separation plate of the present invention significantly reduces opportunities for particle "wall loss".

In another aspect of the present invention, a separation plate in accordance with the present invention may be incorporated in a virtual impact collector. The virtual impact collector comprises the separation plate, a cover plate placed over the nozzles, virtual impactors, and virtual impactor bodies. The cover plate and the first surface of the separation plate at least partially define a chamber therebetween. The inlet ends of the nozzles provide an inlet through which a particle-laden fluid stream enters the chamber. The minor flow passages provide an outlet through which a minor flow exits the chamber. Another outlet is provided to exhaust a major flow from the chamber, such as the orifices and the passageways as described above.

In another aspect of the present invention, the pairs of a nozzle and a virtual impactor may be arranged radially. For example, a plurality of nozzles may be placed radially outward and a plurality of virtual impactors radially inward of the nozzles.

In another aspect of the present invention, the nozzles and the virtual impactors may be provided in various sizes to separate particles of various sizes.

In yet another aspect of the present invention, surfaces of the nozzles, virtual impactors, and virtual impactor bodies may be electrically charged to repel particles that are oppositely charged, to prevent the particles from becoming deposited on the surfaces.

A method of separating particles from a fluid stream using a separation plate of the present invention is also provided. The method includes providing the separation plate of the present invention having a first surface and an opposing second surface, and plural pairs of a nozzle and a virtual impactor provided on the first surface. The method also includes providing a cover plate over the separation plate to form a chamber therebetween, and providing a major flow outlet means to the chamber. The method further includes causing a particle-laden fluid stream to enter the chamber through the inlet ends of the nozzles and flow toward the virtual impactors, wherein a major flow flows around the virtual impactors and is exhausted from the chamber through the major flow outlet, and a minor flow enters the virtual impact voids, advances through the minor flow passages, and exits the chamber therefrom.

In another embodiment of a separation plate in accordance with the present invention, the separation plate includes a first surface and an opposing second surface, and the first surface includes plural pairs of a nozzle and a virtual impactor. As before, the nozzle includes an inlet end and an outlet end, and tapers from the inlet end to the outlet end. The virtual impactor is generally haystack-shaped and includes a convex leading surface. The convex surface faces the outlet end of the nozzle. The convex surface includes an virtual impact void therethrough. The virtual impact void defines a terminal end of a minor flow passage that extends through the separation plate to the second surface.

In operation, particle-laden fluid is caused to enter the inlet ends of the nozzles and flows through the nozzles. The fluid exiting the outlet ends of the nozzles advances toward the virtual impactors. A major flow, as before, flows around the virtual impactors and advances along the first surface. A minor flow enters the virtual impact voids defined through the convex surfaces, and travels through the minor flow passages to the second surface. Accordingly, the separation plate separates a particle-laden fluid stream into a minor flow on the second surface and a major flow on the first surface.

While it is contemplated that the most likely use environment of the present invention will be detection of biological warfare agents in the form of aerosols in an ambient fluid stream, the invention can be used in numerous other environments, such as collection of industrial pollutants in ambient fluid, collection of stack fluids, sampling of fluid in buildings associated with "sick building" syndrome, collection of infectious or disease-causing organisms in hospitals, and the collection of radioactive particles or toxic vapors. It is also contemplated that the present invention may be used for the detection and collection of airborne particles associated with illegal drugs or their precursors.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein:

FIG. 4A is a plan view of another configuration of a separation plate in accordance with the present invention;

DETAILED DESCRIPTION OF THE PREFERRED EMBODIMENT

In the present description, the prefix "micro" is applied generally to components that have submillimeter-sized features. Microcomponents are fabricated using micromachining techniques known in the art, such as micromilling, photolithography, deep ultraviolet (or x-ray) lithography, electrodeposition, electrodischarge machining (EDM), laser ablation, and reactive or nonreactive ion etching.

Also as used hereinafter, the following terms shall have the following definitions:

Particle—any separately identifiable solid, liquid, aerosol, or other component entrained in a fluid stream that has a greater mass than the fluid forming the fluid stream, and is the subject of separation and collection for analysis. For the purposes of the present description, mass density of particles is assumed to be approximately 1 gm/cm$^3$;

Fluid—any fluid susceptible to fluid flow, which may comprise liquids or fluids, and which may entrain foreign particles therein. Unless otherwise noted, fluid shall mean the ambient fluid containing unconcentrated particles for collection, not the fluid into which the particles are concentrated after collection or capture.

Figure 1A:
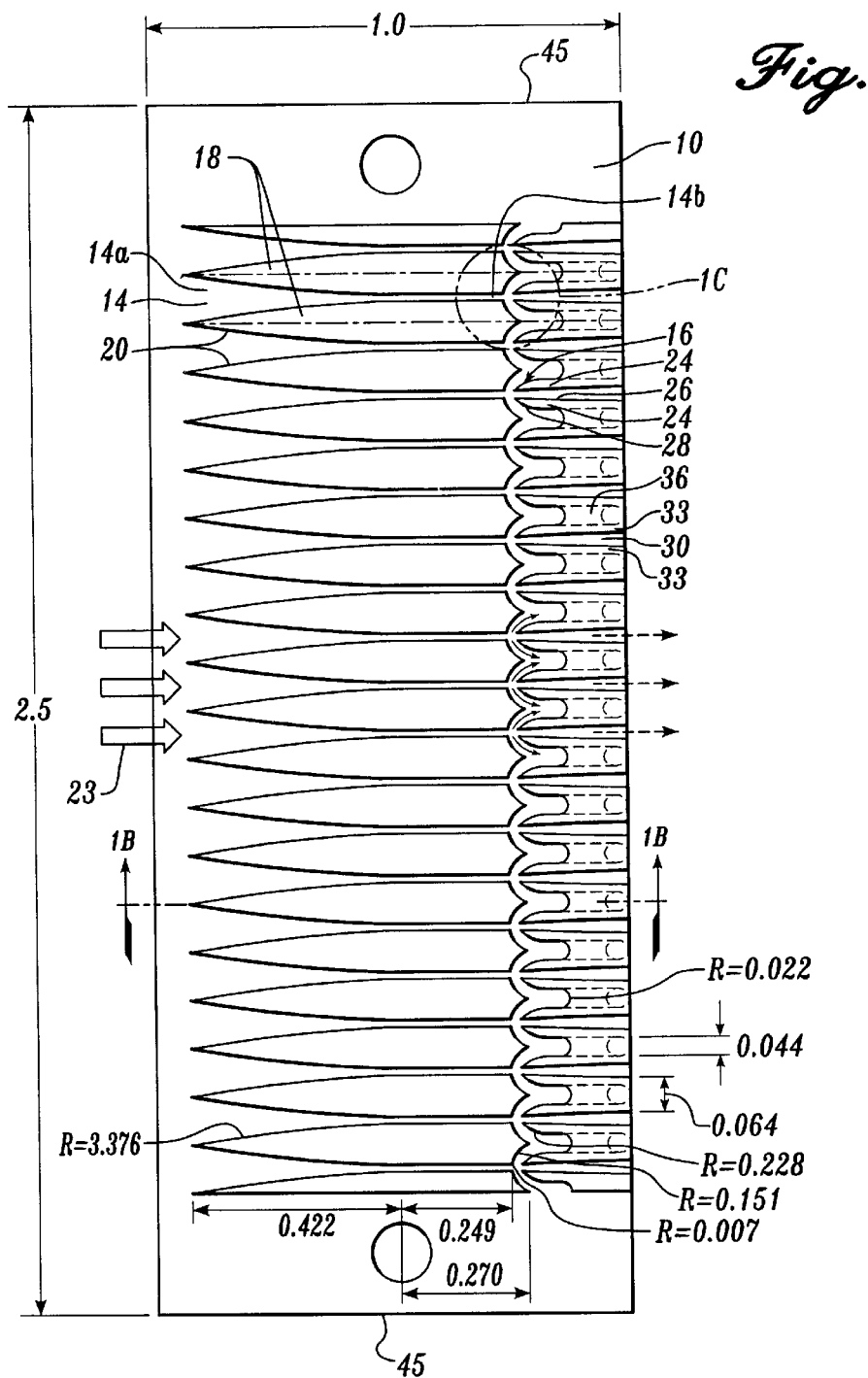
FIG. 1A is a plan view of a separation plate of the present invention.
Figure 1B:
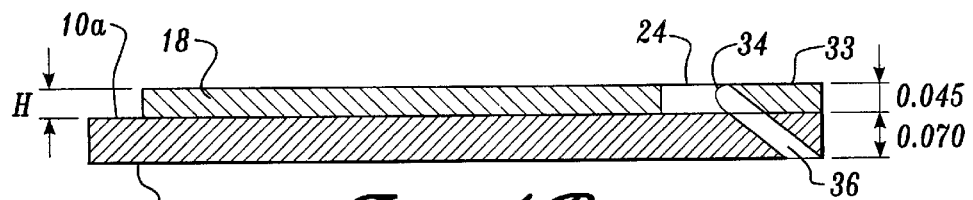
FIG. 1B is a cross-sectional view of the separation plate taken along line 1B—1B of FIG. 1A.
Figure 1C:
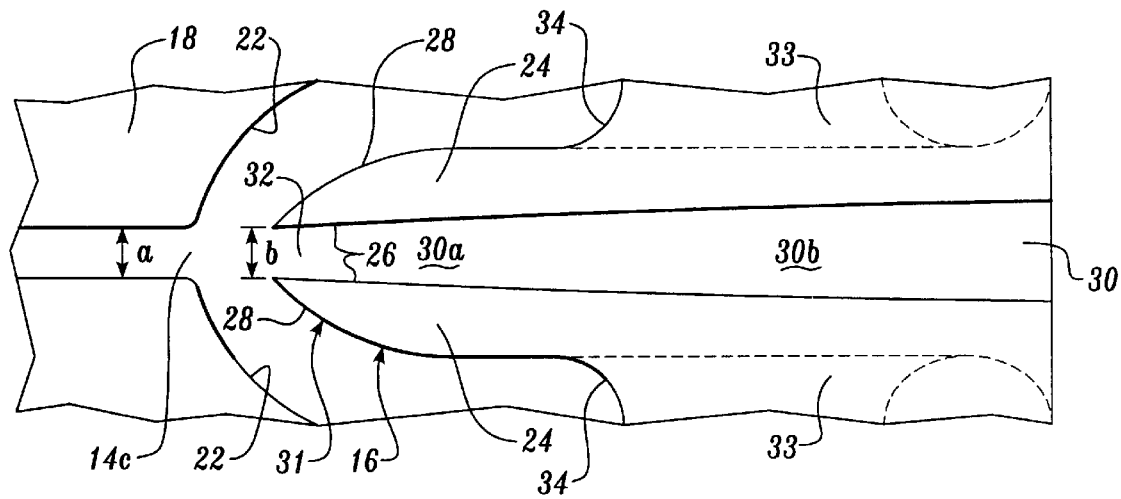
FIG. 1C is an enlarged view of a pair of a nozzle and a virtual impactor at section 1C of FIG. 1A.

FIGS. 1A, 1B, and 1C illustrate the first embodiment of a virtual impact separation plate 10 formed in accordance with the present invention. Separation plate 10 may be formed of any material suitable for micromachining, such as plastics and metals. Separation plate 10 includes a first surface 10a and an opposing second surface 10b. The first surface 10a includes plural pairs of a nozzle 14 and a virtual impactor 16 (FIG. 1C). Each nozzle 14 includes an inlet end 14a and an outlet end 14b, and is defined between adjacent nozzle projections 18 having a height "H" (FIG. 1B). Two nozzle projections 18 cooperate to define one nozzle 14. Each nozzle projection 18 includes two sidewalls 20 that are configured to define one side of a nozzle 14, which generally tapers from inlet end 14a to outlet end 14b. Nozzle projection 18 further includes two generally concave walls 22 at its downstream end that are positioned to provide nozzle projection 18 with a tapered downstream "tail". Throughout the present description, the terms "upstream" and "downstream" are used to refer to the direction of a fluid stream 23 flowing along the separation plate of the present invention.

Each virtual impactor 16 comprises a pair of generally fin-shaped projections 24 having height "H". Fin-shaped projection 24 includes an inner wall 26 and a generally convex outer wall 28. Inner walls 26 of fin-shaped projections 24 in a pair are spaced apart and face each other to define an upstream minor flow passage 30a therebetween. Convex outer walls 28 of the pair of fin-shaped projections 24 cooperatively present a generally convex surface 31 facing the fluid flow direction. Referring specifically to FIG. 1C, an inlet end 32 of upstream minor flow passage 30a defines a virtual impact void through convex surface 31, where "virtual" impaction occurs as more fully described below. A width of outlet end 14b of nozzle 14 is defined as "a", and a width of inlet end 32 of upstream minor flow passage 30a is defined as "b".

The first surface 10a of separation plate 10 may further include a plurality of virtual impactor bodies 33 extending downstream from the downstream ends of adjacent fin-shaped projections 24 of adjacent pairs of virtual impactors 16. Each virtual impactor body 33 includes opposing external walls that extend downstream from the downstream ends of inner walls 26. External walls of adjacent virtual impactor bodies 33 are spaced apart to define a downstream minor flow passage 30b therebetween. Upstream and downstream minor flow passages 30a and 30b are aligned and communicate with each other to form a minor flow passage 30. As illustrated in FIGS. 1A, 1B and 1C, fin-shaped projections 24 of adjacent virtual impactors 16 and a virtual impactor body 33 may be integrally formed. Optionally, an orifice 34 may be defined through virtual impactor body 33 adjacent to the downstream ends of convex outer walls 28 of adjacent virtual impactors 16. Orifices 34 define terminal ends of passageways 36 that extend downward and downstream through separation plate 10 to second surfaces 10b. As more fully described below, orifices 34 and passageways 36 are provided merely as one example of a major flow outlet and, thus, may be replaced with any other suitable major flow outlet.

In operation, particle-laden fluid stream 23 is caused to enter inlet ends 14a of nozzles 14. Nozzles 14 aerodynamically focus and accelerate particles entrained in fluid stream 23. The aerodynamically focused fluid stream 23 exiting outlet ends 14b of nozzles 14 advances to convex surfaces 31 of virtual impactors 16. A major portion (at least 50%, preferably at least approximately 90%) of fluid stream 23 containing a minor portion (less than about 50%) of particles above a certain particle diameter size, or a "cut size" (hereinafter "major flow") changes direction to avoid obstruction presented by convex surfaces 31, as indicated by solid arrows. Concave walls 22 of nozzle projections 18 and convex outer walls 28 of fin-shaped projections 24 cooperate to direct the major flow toward the upstream end of virtual impactor bodies 33. Bodies 33 prevent the major flow from further advancing. When orifices 34 are provided through bodies 33, the major flow enters orifices 34 and travels through passageways 36 to second surface 10b of separation plate 10, where it can be exhausted or processed further. A minor portion (less than 50%, preferably less than approximately 10%) of fluid stream 23 containing a major portion (at least about 50%) of particles above a certain "cut size" (hereinafter "minor flow") is collected near a "dead fluid" zone or a zone of stagnant air created adjacent to the convex surfaces 31 of virtual impactors 16. The major portion of the particles entrained in the minor flow "virtually" impact the virtual impact voids, or the inlet ends 32 of upstream minor flow passages 30a, and enter the minor flow passages 30. The minor flow travels through minor flow passages 30 and exits therefrom as indicated by dotted arrows, where the particles can be collected, analyzed, or processed further.

Nozzles 14 contribute very little to particle loss because they have a long tapering profile, which prevents particle deposition thereon. The long tapering profile of the nozzles 14 also serves to reduce turbulence and align and accelerate particles. Because nozzles 14 aerodynamically focus and accelerate particles in a fluid stream, virtual impactors 16 placed downstream of nozzles 14 are able to separate particles very efficiently. By improving the particle separation efficiency of each of virtual impactors 16, the present invention allows for employing only one layer or row of virtual impactors 16 for completing particle separation, which eliminates the chances of particles getting lost onto surfaces of additional layers or rows of virtual impactors. The present invention further reduces particle loss onto inner surfaces of minor flow passages, by allowing minor flows to advance straight through the minor flow passages upon virtual impaction, without having to change its flow direction.

A separation plate 10 configured in accordance with the dimensions (all in inches) shown in FIGS. 1A and 1B is designed to have a cut size of 7 microns at a flow rate of 25 liters per minute (LPM). The term "cut size" means a particle diameter at which 50% of the particles of that diameter flowing along the first surface of a separation plate are separated from a fluid stream, and mostly exhausted through the minor flow passages. For particles having a diameter above the cut size, preferably more than 50% of the particles flowing along the separation plate are separated. It should be understood that those skilled in the art may readily optimize separation plate 10 of the present invention to meet a specific "cut size" requirement at a certain flow rate. For example, the "cut size" of a separation plate may be modified by scaling up or down the various structures provided on the separation plate; larger nozzles with proportionally larger virtual impactors are useful in separating larger particles, while conversely smaller nozzles with proportionally smaller virtual impactors are useful in separating smaller particles. The "cut size" of a separation plate may also be modified by adjusting a flow rate through the separation plate. For particles having 1- to 3-micron diameters, it has been found that making "a" greater than "b" generally reduces recirculation of a minor flow upon entering minor flow passage 30, which is preferable for efficiently separating a minor flow. For larger particles, it may be preferable to make "a" smaller than "b" to reduce pressure drop.

Figure 1D:
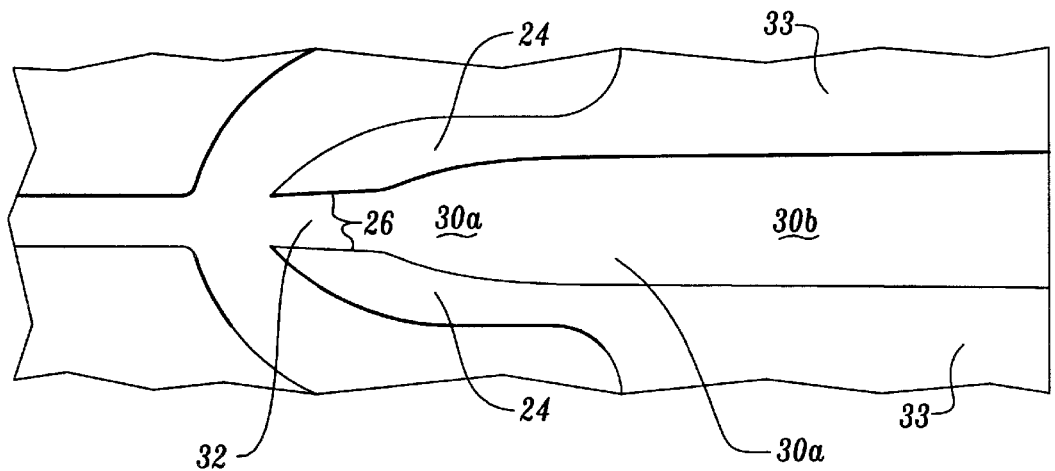
FIG. 1D is an enlarged view of another configuration of a pair of a nozzle and a virtual impactor.

FIG. 1D illustrates modified configurations of a pair of a nozzle 14 and a virtual impactor 16, wherein inner walls 26 of fin-shaped projections 24 include a generally concave surface. Accordingly, the width of upstream minor flow passage 30a expands from inlet end 32 toward the downstream minor flow passage 30b defined between the external walls of adjacent virtual impactor bodies 33. This configuration is advantageous in preventing recirculation of the minor flow upon entering upstream minor flow passage 30a, and also in reducing particle loss onto the inner walls 26.

A separation plate of the present invention may be easily modified to process virtually any volume of fluid stream at any flow rate, by varying the number of nozzles 14 and virtual impactors 16 provided on the separation plate. Furthermore, the throughput of separation plate 10 may be almost indefinitely modifiable by increasing or decreasing height "H" of nozzles 14, virtual impactors 16, and virtual impactor bodies 33. It should be noted that height "H" of a separation plate of the invention can be freely increased without a significant increase in particle loss. This is made possible by the present design that allows minor flows to advance straight through without experiencing any deflected path.

Figure 2A:
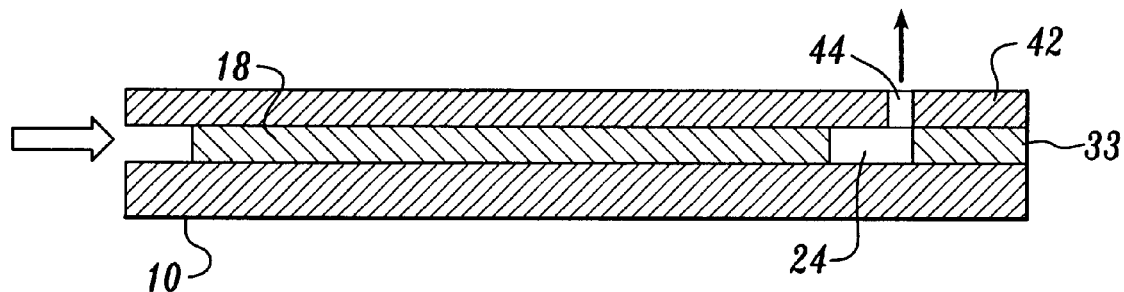
FIG. 2A is a schematic cross-sectional view of a virtual impact collector incorporating another configuration of a separation plate of the present invention.

Separation plate 10 of the present invention may be readily incorporated into various particle separation/concentration apparatus. Referring to FIG. 2, for example, a virtual impact collector may be formed by placing a cover plate 42 over nozzle projections 18, fin-shaped projections 24, and virtual impactor bodies 33 provided on first surface 10a. The cover plate 42 and first surface 10a cooperatively define a chamber. Inlet ends 14a of nozzles 14 provide an inlet through which a particle-laden fluid stream may enter the chamber. Minor flow passages 30 provide an outlet through which a minor flow may exit the chamber. An outlet through which a major flow may exit the chamber may be provided in various ways. For example, as in FIGS. 1A and 1B, a plurality of orifices 34 defining terminal ends of passageways 36 may be provided through virtual impactor bodies 33. Alternatively, as in FIG. 2A, cover plate 42 may include a plurality of holes 44 provided therethrough. Holes 44 are configured and arranged so that, when cover plate 42 is mated with separation plate 10, holes 44 are placed between virtual impactors 16 adjacent the upstream end of virtual impactor bodies 33 to exhaust major flows flowing around virtual impactors 16 and being blocked by bodies 33, as indicated by an arrow. It should be understood that, in operating the virtual impact collector as described above, those skilled in the art can provide a suitable flow subsystem for causing a fluid stream to flow through the chamber.

Figure 2B:
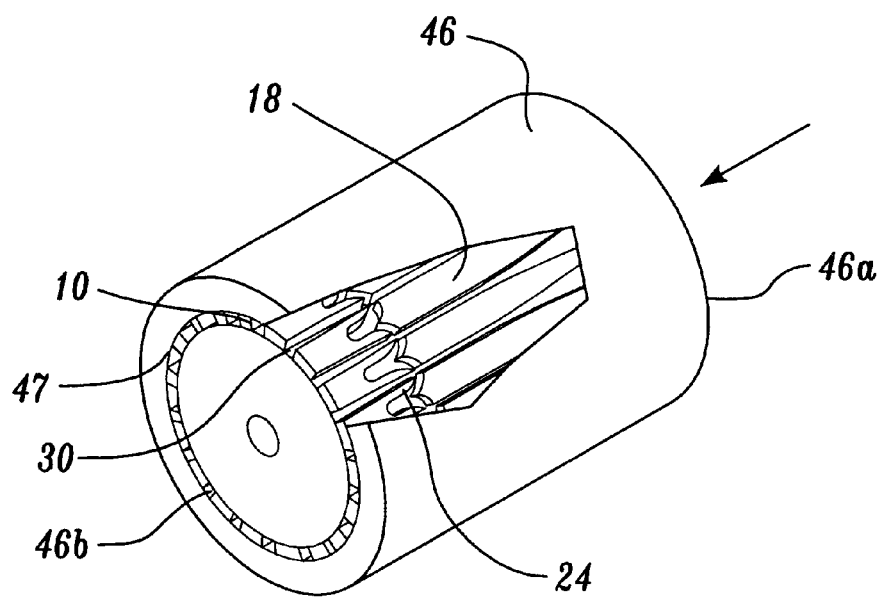
FIG. 2B is a schematic perspective view of an alternative configuration of a virtual impact collector in accordance with the present invention.

A further example of a virtual impact collector formed in accordance with the present invention is schematically illustrated in FIG. 2B. In this embodiment, separation plate 10 of FIG. 1A is joined at its opposing edges 45 to form a cylinder. The second surface of separation plate 10 forms the inner surface of the cylinder. The cylindrical separation plate 10 is coaxially slid into a tube 46 having two open ends 46a, and 46b to form an annular chamber 47 therebetween. As before, a suitable major flow outlet is provided (not shown). In operation, particle-laden fluid streams enter the chamber 47 through the inlet ends of nozzles defined between nozzle projections 18 adjacent open end 46a. Minor flow passages 30 provide an outlet through which a minor flow may exit the chamber 47. A suitably provided major flow outlet deflects a major flow to either or both of the inner surface of the cylindrical separation plate 10 or the outer surface of the tube 46.

Figure 3A:
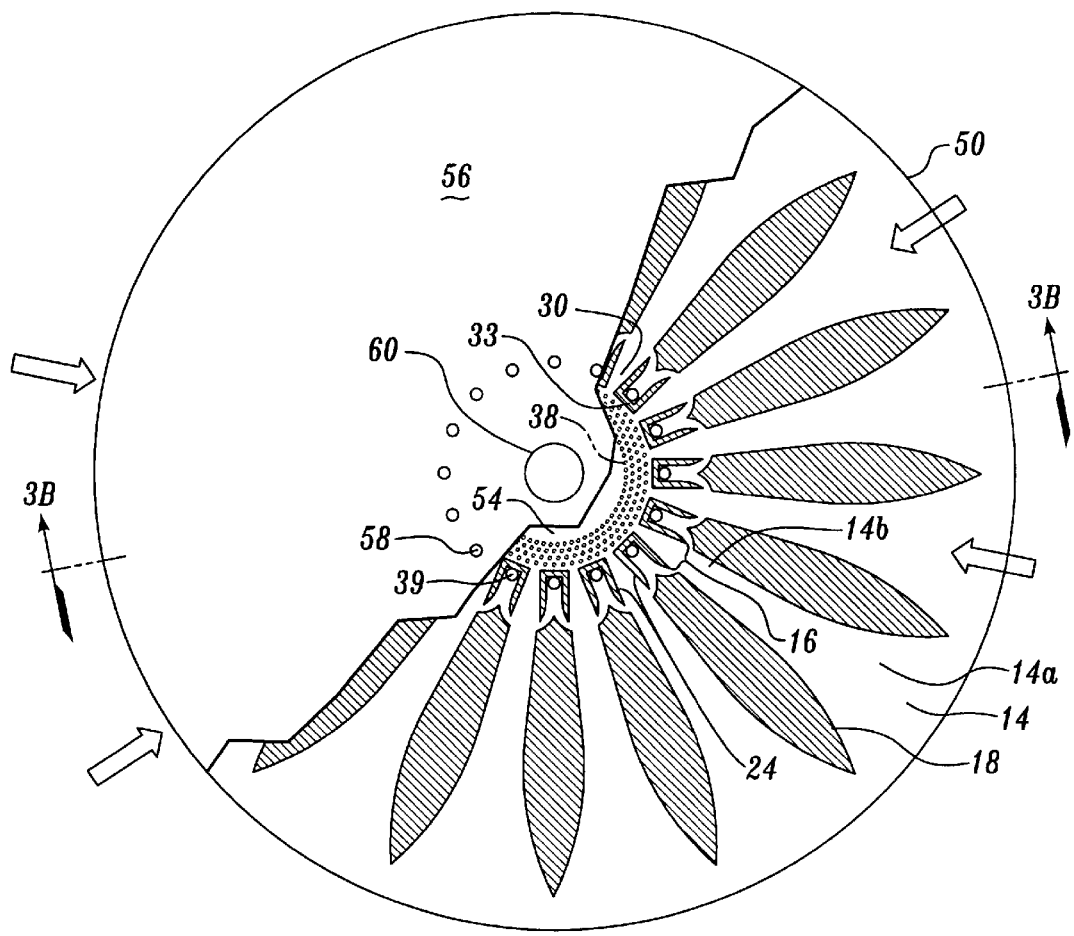
FIG. 3A is a plan view of a virtual impact collector incorporating plural pairs of a nozzle and a virtual impactor arranged radially.
Figure 3B:
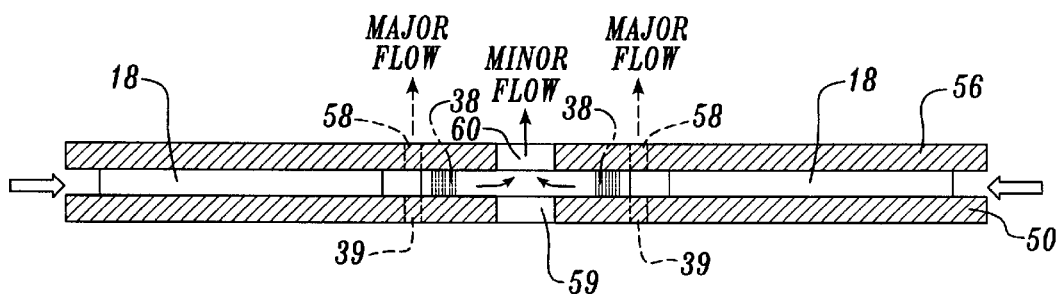
FIG. 3B is a cross-sectional view of the virtual impact collector taken along line 3B—3B of FIG. 3A.

FIGS. 3A and 3B schematically illustrate a virtual impact collector incorporating another configuration of a separation plate 50 of the present invention and a cover plate 56.

Separation plate 50 includes plural pairs of a nozzle 14 and virtual impactor 16 that is placed radially inward of nozzle 14. As before, nozzle 14, having an inlet end 14a and an outlet end 14b, is defined between adjacent nozzle projections 18. Virtual impactor 16 comprises a pair of fin-shaped projections 24 provided downstream of, and radially inward of, outlet end 14b of each nozzle 14. As before, fin-shaped projections 24 in each pair are spaced apart and define minor flow passage 30 therebetween. Also as before, a plurality of virtual impactor bodies 33 in the form of a wall are provided to extend between the downstream ends of fin-shaped projections 24 of adjacent virtual impactors 16. Optionally, a plurality of holes 39 may be provided through separation plate 50 radially outward of virtual impactor bodies 33 between the fin-shaped projections 24 of adjacent virtual impactors 16. Virtual impactors 16 and bodies 33 together define a central minor flow collection portion 54. A plurality of impactor pillars 38 may be placed radially inward and downstream of minor flow passages 30, within central minor flow collection portion 54. Impactors 38 are employed to receive a minor flow to collect particles thereon, as more fully described below. Optionally, a minor flow outlet 59 may be provided through separation plate 50 near the center of central minor flow collection portion 54.

Separation plate 50 described above may be combined with cover plate 56 to form a virtual impact collector. Cover plate 56 is configured to mate with separation plate 50 to define a chamber therebetween. Optionally, cover plate 56 may include holes 58 that are configured and arranged so that when separation plate 50 and cover plate 56 are combined, holes 58 are aligned to coincide with holes 39 defined through separation plate 50. Further optionally, cover plate 56 may include minor flow outlet 60 defined therethrough. Minor flow outlet 60 is configured so that when cover plate 56 and separation plate 50 are combined, minor flow outlet 60 of cover plate 56 aligns with minor flow outlet 59 of separation plate 50. Holes 39 of separation plate 50 and/or holes 58 of cover plate 56 provide a major flow outlet to the chamber. Minor flow outlet 59 of separation plate 50 and/or minor flow outlet 60 of cover plate 56 provide a minor flow exhaust to the chamber.

In operation, particle-laden fluid streams enter nozzles 14 through inlet ends 14a and advance radially inward. When aerodynamically focused fluid streams advance toward virtual impactors 16, they are separated into a minor flow and a major flow as described earlier. The major flow flows around virtual impactors 16, is blocked by bodies 33, and exhausted through either or both of holes 39 in separation plate 50 and holes 58 in cover plate 56. The minor flow advances through minor flow passages 30 into central minor flow collection portion 54. When impactors 38 are provided, some of the particles entrained in the minor flow may impact and become deposited on impactors 38. The particles collected on impactors 38 may be subsequently collected, for example, by washing impactors 38 with a small amount of liquid to capture the particles therein. An example of impactors suitable for use in conjunction with the present invention can be found in copending U.S. patent application, Ser. No. 09/191,979, filed concurrently herewith, and assigned to the same assignee, which is herein expressly incorporated by reference (Attorney Docket No. MESO-1-12864). The minor flow may be exhausted from central minor flow collection portion 54 through either or both of minor flow outlets 59 and 60.

When both minor flow outlets 59 and 60, and both holes 39 and 58 are provided, as illustrated in FIG. 3B, a plurality of the virtual impact collectors described above may be stacked together to process large amounts of fluid streams. The stacked virtual impact collectors include a common minor flow exhaust conduit comprising minor flow outlets 59 and 60, and a common major flow exhaust conduit comprising holes 39 and 58.

Figure 4C:
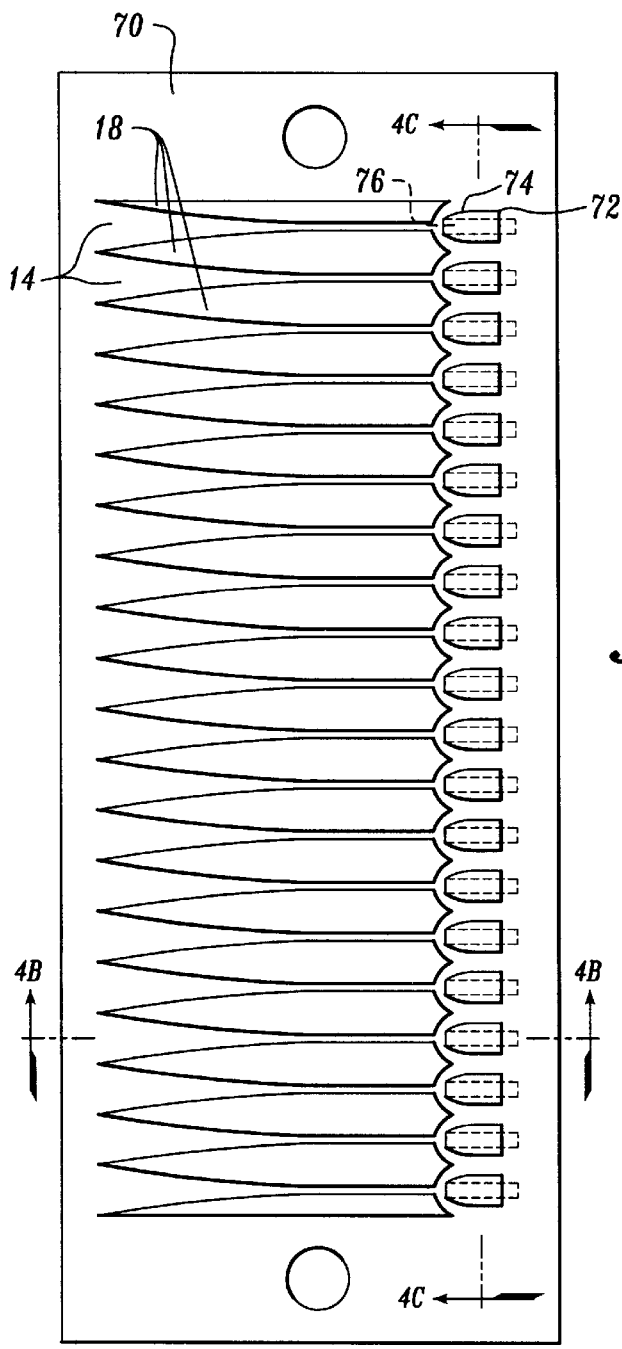
FIG. 4C is a cross sectional view of the separation plate taken along line 4C—4C of FIG. 4A.
Figure 4C:
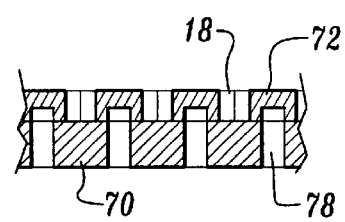
Figure 4B:
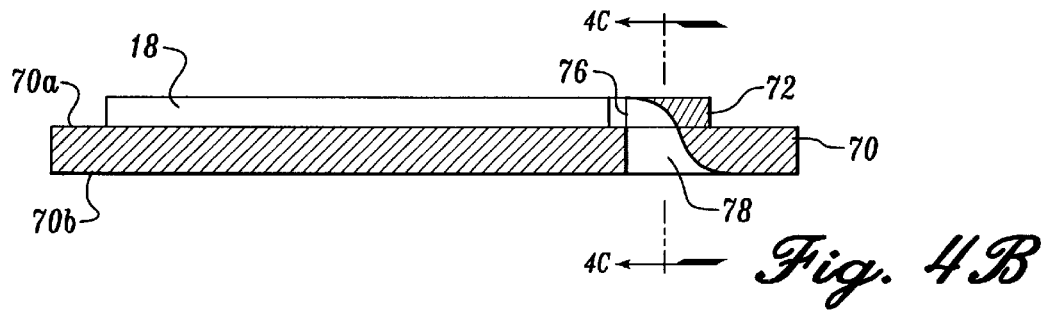
FIG. 4B is a cross-sectional view of the separation plate taken along line 4B—4B of FIG. 4A.

FIGS. 4A, 4B, and 4C illustrate another embodiment of a separation plate 70 in accordance with the present invention. As in the first embodiment, separation plate 70 includes a first surface 70a and an opposing second surface 70b. First surface 70a is provided with a plurality of nozzle projections 18 that define nozzles 14 therebetween. As before, nozzle 14 tapers from an inlet end 14a to an outlet end 14b. Downstream of each outlet end 14b, a generally haystack-shaped virtual impactor projection 72 is provided. Virtual impactor projection 72 includes a convex leading surface 74 facing the fluid flow. A virtual impact void 76 is provided through convex surface 74 near its apex. Virtual impact void 76 defines a terminal end of a minor flow passage 78 that extends down and through separation plate 70. Minor flow passage 78 and virtual impact void 76 may be formed by, for example, boring an end-mill through second surface 70b of separation plate 70. Alternatively, minor flow passage 78 and virtual impact void 76 may be formed by drilling a hole through separation plate 70. When drilling a hole, minor flow passage 78 preferably passes through separation plate 70 at an acute angle so that a minor flow containing a major portion of particles will avoid sharp changes in direction upon entering virtual impact void 76. It should be noted that the longer the minor flow passage 78, the more particles may be deposited on the inner surfaces of minor flow passage 78. Therefore, while the angle of minor flow passage 78 should be as acute as possible, the length of minor flow passage 78 cannot be indefinitely long. The optimum combination of the angle and the length of minor flow passage 78 is to be determined based partly on the limitations imposed by the available micromachining methods. An angle of approximately between 15° and 45°, which is possible with currently available micromachining methods, should provide satisfactory results.

In operation, particle-laden fluid streams flow along first surface 10a through nozzles 14 and advance toward convex surfaces 74 of virtual impactor projections 72. Major flows flow around projections 72 to avoid obstruction presented by convex surfaces 74, and continue along first surface 70a. Minor flows are collected in a zone of stagnant fluid created near convex surfaces 74, and enter virtual impact voids 76 defined through convex surfaces 74. The minor flows travel through minor flow passages 78 to second surface 70b, where they can be collected, analyzed, or processed further in any other manner. Thus, unlike separation plates 10 and 50 of previous embodiments, separation plate 70 of the present embodiment separates a particle-laden fluid stream into a minor flow on the second surface, and a major flow on the first surface.

In any of the above-described embodiments of the separation plate, it has been found that electrically charging various structures on the separation plate improves particle collection efficiency of the plate. Specifically, the exterior surfaces of the nozzles and various virtual impactors may include a coating of any suitable conductive material, such as aluminum. A thickness of the coating may range approximately between 0.025 mm and 0.05 mm, although other thicknesses may be suitable. A conductive lead having a width of approximately 0.12 mm and a thickness or approximately between 0.025 mm and 0.05 mm may be provided to connect with each coated structure. Alternatively, the entire first surface of the separation plate may be coated with a conductive material. Further alternatively, an entire separation plate, or at least a portion of a separation plate, or an entire virtual impact collector including a cover plate of the invention may be constructed of conductive material. The coated portions of the first surface and projections, or any elements made of conductive material can be connected to an electric circuit including a power source to supply current, e.g., direct current.

As many particles include an intrinsic net charge, the conductive surfaces may be charged to repel the particles, typically with a few volts. This serves to prevent the particles from becoming deposited on the conductive surfaces and, thus, to efficiently forward a major portion of the particles for collection or analysis. Those skilled in the art can determine the level of charge to be applied in each application, depending on the type of particles to be separated and the effect of the charge on the flow properties of the particles.

While the preferred embodiments of the invention have been illustrated and described, it will be appreciated that various changes can be made therein without departing from the spirit and scope of the invention.

The embodiments of the invention in which an exclusive property or privilege is claimed are defined as follows:

1. A separation plate for separating particles from a fluid stream having a first surface and an opposing second surface, the first surface including:

plural pairs of a nozzle and a virtual impactor, the nozzle having an inlet end and an outlet end and tapering from the inlet end to the outlet end, the virtual impactor comprising a pair of fin-shaped projections, each fin-shaped projection having a convex outer wall and an inner wall, the inner walls of the pair of fin-shaped projections facing each other and being spaced apart to define an upstream minor flow passage therebetween, the convex outer walls of the pair of fin-shaped projections cooperatively presenting a convex surface defining a virtual impact void therethrough, the virtual impact void defining an inlet end of the upstream minor flow passage, the convex surface facing the outlet end of each nozzle such that the nozzle and the upstream minor flow passage are generally aligned with each other.

2. The separation plate of claim 1, further comprising a virtual impactor body extending between downstream ends of fin-shaped projections of adjacent virtual impactors.

3. The separation plate of claim 1, wherein the virtual impactor body extends downstream of the fin-shaped projections and includes opposing external walls, the external walls of adjacent impactor bodies being spaced apart to define a downstream minor flow passage that is aligned with and communicates with the upstream minor flow passage.

4. The separation plate of claim 1, further comprising a plurality of orifices defined between adjacent virtual impactors, the orifices defining terminal ends of passageways extending through the separation plate.

5. The separation plate of claim 1, wherein a width of the outlet end of the nozzle is greater than a width of the inlet end of the upstream minor flow passage.

6. The separation plate of claim 1, wherein a width of the outlet end of the nozzle is smaller than a width of the inlet end of the upstream minor flow passage.

7. The separation plate of claim 1, wherein the plural pairs of a nozzle and a virtual impactor are arranged linearly, a plurality of nozzles arranged in a row and a plurality of virtual impactors arranged in an adjacent row.

8. The separation plate of claim 1, wherein the plural pairs of a nozzle and a virtual impactor are arranged radially, a plurality of nozzles arranged in a circle radially outward and a plurality of virtual impactors arranged in a circle radially inward of the plurality of nozzles.

9. The separation plate of claim 1, further comprising a plurality of impactors placed downstream of the virtual impactors.

10. The separation plate of claim 1, wherein the inner walls of the pair of fin-shaped projections include a generally concave surface so that the width of the upstream minor flow passage generally expands from upstream to downstream.

11. The separation plate of claim 1, further comprising:
a conductive material on the first surface of the separation plate including the surfaces of the nozzles and the virtual impactors; and
a circuit including a power source for electrically charging the conductive material.

12. The separation plate of claim 1, wherein at least a portion of the separation plate is made of conductive material, and further comprising a circuit including a power source for electrically charging the conductive material.

13. The separation plate of claim 1, further comprising:
a cover plate placed over the first surface of the separation plate to sandwich the nozzles and the virtual impactors therebetween; and
a chamber at least partially defined by the cover plate and the first surface.

14. The separation plate of claim 13, further comprising a flow subsystem for inducing flow of the fluid stream through the chamber.

15. The separation plate of claim 13, wherein the separation plate is a cylinder, the second surface of the separation plate forming the inner surface of the cylinder.

16. The separation plate of claim 13, wherein at least a portion of the cover plate and the separation plate is made of conductive material, and further comprising a circuit including a power source for electrically charging the conductive material.

17. A method of separation of particles from a fluid stream, comprising:
providing a separation plate having a first surface and an opposing second surface, the first surface including plural pairs of a nozzle and a virtual impactor, the nozzle having an inlet end and an outlet end and tapering from the inlet end to the outlet end to lessen the fluid turbulence, the virtual impactor comprising a pair of fin-shaped projections, each fin-shaped projection having a convex outer wall and an inner wall, the inner walls of the pair of fin-shaped projections facing each other and being spaced apart to define an upstream minor flow passage therebetween, the convex outer walls of the pair of fin-shaped projections cooperatively presenting a convex surface including a virtual impact void therethrough, the void defining an inlet end of the upstream minor flow passage, the convex surface facing the outlet end of each nozzle such that the nozzle and the upstream minor flow passage are generally aligned with each other;
providing a cover plate over the nozzles and virtual impactors to form a chamber between the cover plate and the first surface;
providing a major flow outlet to the chamber, and causing the fluid stream to enter the chamber through the inlet ends of the nozzles and advance toward the virtual impactors, wherein a major portion of the fluid stream containing a minor portion of the particles flows around the virtual impactors, and is exhausted from the chamber through the major flow outlet, and a minor portion of the fluid stream containing a major portion of the particles enters the virtual impact voids, and exits the chamber through minor flow passages.

18. The method of claim 17, wherein the major flow outlet is provided in the form of a plurality of orifices between virtual impactors, each orifice defining a terminal end of a passageway extending through the separation plate.

19. The method of claim 17, wherein the major flow outlet is provided in the form of a plurality of holes provided through the cover plate.

20. The method of claim 17, wherein the plural pairs of a nozzle and a virtual impactor are arranged linearly, a plurality of nozzles arranged in a row and a plurality of virtual impactors arranged in an adjacent row.

21. The method of claim 17, wherein the plural pairs of a nozzle and a virtual impactor are arranged radially, a plurality of nozzles arranged in a circle radially outward and a plurality of virtual impactors arranged in a circle radially inward of the plurality of nozzles.

22. The method of claim 17, further comprising collecting the minor portion of the fluid stream exiting the chamber through the minor flow passages.

23. The method of claim 17, further comprising electrically charging at least a portion of the separation plate and the cover plate.

24. The method of claim 23, wherein a plurality of impactors are provided downstream of the virtual impactors for collecting the minor portion of the fluid stream.

25. A separation plate for separating particles from a fluid stream having a first surface and an opposing second surface, the first surface including:
plural pairs of a nozzle and a virtual impactor, the nozzle having an inlet end and an outlet end and tapering from the inlet end to the outlet end, the virtual impactor is generally haystack-shaped having a convex surface facing the outlet end of each nozzle, the convex surface defining an virtual impact void therethrough, the virtual impact void defining a terminal end of a minor flow passage that communicates between the first and second surfaces.

26. The separation plate of claim 25, wherein the plural pairs of a nozzle and a virtual impactor are arranged linearly, a plurality of nozzles arranged in a row and a plurality of virtual impactors arranged in an adjacent row.

* * * * *